(12) United States Patent
Brown et al.

(10) Patent No.: US 7,670,383 B1
(45) Date of Patent: *Mar. 2, 2010

(54) PUBIC CATCH

(75) Inventors: David R Brown, Warsaw, IN (US);
Mark A Bollinger, Fort Wayne, IN (US); Brian M May, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 1299 days.

This patent is subject to a terminal disclaimer.

(21) Appl. No.: 10/838,885

(22) Filed: May 4, 2004

(51) Int. Cl.
*A61F 2/32* (2006.01)
(52) U.S. Cl. .................................... 623/22.22
(58) Field of Classification Search ............. 623/16.11, 623/18.11, 22.11, 22.21, 22.22
See application file for complete search history.

(56) References Cited

U.S. PATENT DOCUMENTS

| | | |
|---|---|---|
| 408,080 A | 7/1889 | Carroll |
| 583,455 A | 6/1897 | Bush |
| 1,217,637 A | 2/1917 | Rink |
| 2,397,545 A | 4/1946 | Hardinge |
| 3,067,740 A * | 12/1962 | Haboush ............ 623/22.15 |
| 3,740,769 A * | 6/1973 | Haboush ............ 623/22.36 |
| 3,947,897 A | 4/1976 | Owens |
| 4,016,874 A | 4/1977 | Maffei et al. |
| 4,080,666 A | 3/1978 | Fixel |
| 4,129,903 A | 12/1978 | Huggler |
| 4,158,895 A | 6/1979 | Reswick et al. |
| 4,245,360 A | 1/1981 | Brinckmann et al. |
| 4,262,665 A | 4/1981 | Roalstad et al. |
| 4,314,381 A | 2/1982 | Koeneman |
| 4,502,160 A | 3/1985 | Moore et al. |
| 4,547,912 A | 10/1985 | Sherva-Parker |
| 4,586,932 A | 5/1986 | Scales |
| 4,621,629 A | 11/1986 | Koeneman |
| 4,623,352 A * | 11/1986 | Oh .................... 623/22.28 |
| 4,644,943 A | 2/1987 | Thompson et al. |
| 4,673,407 A | 6/1987 | Martin |

(Continued)

FOREIGN PATENT DOCUMENTS

DE 3605630 9/1987

(Continued)

OTHER PUBLICATIONS

"Reconstruction of the Pelvis After Resection of Tumors About the Acetabulum," Clinical Orthopaedics and Related Research, No. 409, pp. 209-217. Copyright 2003 Lippincott Williams & Wilkins, Inc.

(Continued)

*Primary Examiner*—Anu Ramana
(74) *Attorney, Agent, or Firm*—Harness, Dickey

(57) ABSTRACT

A prosthetic device for replacement of a hip bone that includes an acetabular component configured to connect to a femoral implant and a pubis member. The pubis member connects to the acetabular component and includes a clamping portion that is configured to attach to an opposed healthy pubis bone. The pubis member further includes a worm or other clamping method drive that is configured to tighten the clamping portion against the opposed healthy pubis bone thereby providing stability to the prosthetic hip bone and avoiding the use of bone screws in the opposed healthy pubis bone.

21 Claims, 13 Drawing Sheets

U.S. PATENT DOCUMENTS

| | | | |
|---|---|---|---|
| 4,682,590 | A | 7/1987 | Kothmann |
| 4,781,720 | A | 11/1988 | Sherva-Parker |
| 4,822,366 | A | 4/1989 | Bolesky |
| 4,827,918 | A | 5/1989 | Olerud |
| 4,883,489 | A | 11/1989 | Grundei et al. |
| 4,892,551 | A | 1/1990 | Haber |
| 4,904,264 | A | 2/1990 | Scheunemann |
| 4,923,472 | A | 5/1990 | Ugolini et al. |
| 4,938,768 | A | 7/1990 | Wu |
| 4,946,459 | A | 8/1990 | Bradshaw et al. |
| 4,947,502 | A | 8/1990 | Engelhardt |
| 4,955,910 | A | 9/1990 | Bolesky |
| 4,959,064 | A | 9/1990 | Engelhardt |
| 4,959,072 | A | 9/1990 | Morscher et al. |
| 4,986,834 | A | 1/1991 | Smith et al. |
| 5,007,935 | A | 4/1991 | Vincent et al. |
| 5,007,936 | A | 4/1991 | Woolson |
| 5,030,220 | A | 7/1991 | Howland |
| 5,035,712 | A | 7/1991 | Hoffman |
| 5,057,103 | A | 10/1991 | Davis |
| 5,071,435 | A | 12/1991 | Fuchs et al. |
| 5,108,398 | A | 4/1992 | McQueen et al. |
| 5,112,333 | A | 5/1992 | Fixel |
| 5,133,760 | A | 7/1992 | Petersen et al. |
| 5,156,625 | A | 10/1992 | Marchetti et al. |
| 5,180,383 | A | 1/1993 | Haydon |
| 5,181,928 | A | 1/1993 | Bolesky et al. |
| 5,197,989 | A | 3/1993 | Hinckfuss et al. |
| 5,201,881 | A | 4/1993 | Evans |
| 5,267,999 | A | 12/1993 | Olerud |
| 5,281,226 | A | 1/1994 | Davydov et al. |
| 5,326,360 | A | 7/1994 | Kotz et al. |
| 5,326,367 | A | 7/1994 | Robioneck |
| 5,326,368 | A | 7/1994 | Collazo |
| 5,334,184 | A | 8/1994 | Bimman |
| 5,352,227 | A | 10/1994 | O'Hara |
| 5,356,410 | A | 10/1994 | Pennig et al. |
| 5,358,524 | A | 10/1994 | Richelsoph |
| 5,389,107 | A | 2/1995 | Nassar et al. |
| 5,411,504 | A | 5/1995 | Vilas |
| 5,507,747 | A | 4/1996 | Yuan et al. |
| 5,507,827 | A | 4/1996 | Grundei et al. |
| 5,549,692 | A | 8/1996 | Hauser et al. |
| 5,658,288 | A | 8/1997 | Kim |
| 5,743,908 | A | 4/1998 | Kim |
| 5,800,553 | A | 9/1998 | Albrektsson et al. |
| 5,800,557 | A | 9/1998 | Elhami |
| 5,824,078 | A | 10/1998 | Nelson et al. |
| 5,827,285 | A | 10/1998 | Bramlet |
| 5,871,540 | A | 2/1999 | Weissman et al. |
| 5,882,351 | A * | 3/1999 | Fox .............. 606/63 |
| 5,928,232 | A | 7/1999 | Howland et al. |
| 5,941,881 | A * | 8/1999 | Barnes .............. 606/71 |
| 5,951,555 | A | 9/1999 | Rehak et al. |
| 5,981,828 | A | 11/1999 | Nelson et al. |
| 6,051,007 | A | 4/2000 | Hogendijk et al. |
| 6,162,257 | A | 12/2000 | Gustilo et al. |
| 6,197,065 | B1 | 3/2001 | Martin et al. |
| 6,200,317 | B1 | 3/2001 | Aalsma et al. |
| 6,273,891 | B1 * | 8/2001 | Masini .............. 606/91 |
| 6,293,971 | B1 | 9/2001 | Nelson et al. |
| 6,336,929 | B1 | 1/2002 | Justin |
| 6,336,941 | B1 | 1/2002 | Subba Rao et al. |
| 6,387,097 | B1 | 5/2002 | Alby |
| 6,458,161 | B1 | 10/2002 | Gibbs et al. |
| 6,482,238 | B1 | 11/2002 | Grundei |
| 6,485,522 | B1 | 11/2002 | Grundei |
| 6,508,841 | B2 | 1/2003 | Martin et al. |
| 6,579,294 | B2 | 6/2003 | Robioneck |
| 6,656,184 | B1 | 12/2003 | White et al. |
| 6,712,855 | B2 | 3/2004 | Martin et al. |
| 6,740,089 | B2 | 5/2004 | Haider |
| 6,786,910 | B2 * | 9/2004 | Cohen et al. .............. 606/71 |
| 6,840,959 | B2 | 1/2005 | Treacy et al. |
| 2001/0051831 | A1 | 12/2001 | Subba Rao et al. |
| 2003/0028249 | A1 | 2/2003 | Baccelli et al. |
| 2003/0109878 | A1 | 6/2003 | Grundei |
| 2003/0130659 | A1 | 7/2003 | Haider |
| 2003/0195636 | A1 | 10/2003 | Coop |
| 2004/0138663 | A1 | 7/2004 | Kosashvili et al. |
| 2004/0148021 | A1 * | 7/2004 | Cartledge et al. .......... 623/2.37 |
| 2004/0172138 | A1 | 9/2004 | May et al. |
| 2006/0241779 | A1 | 10/2006 | Lakin |

FOREIGN PATENT DOCUMENTS

| | | |
|---|---|---|
| DE | 293485 | 9/1991 |
| DE | 199 31 882 | 5/2001 |
| FR | 2519248 | 12/1981 |
| FR | 2519248 | 7/1983 |
| SU | 1181652 | 9/1985 |
| WO | WO 96/35387 | 11/1996 |
| WO | WO 98/29058 | 7/1998 |
| WO | WO 00/27298 | 5/2000 |
| WO | WO 01/43652 | 6/2001 |
| WO | WO 02/071962 | 9/2002 |

OTHER PUBLICATIONS

European Search Report mailed Jul. 21, 2005 for pending European Application No. EP05251364.

Aboulafia, Albert J., et al., "Reconstruction Using the Saddle Prosthesis Following Excision of Primary and Metastic Periacetabular Tumors" (1995), Clinical Orthopaedics and Related Research, No. 314, pp. 203-213.

Mueckley, Thomas, et al., "Compression Nailing of Long Bones", European Journal of Trauma (2003) No. 3 pp. 113-128.

* cited by examiner

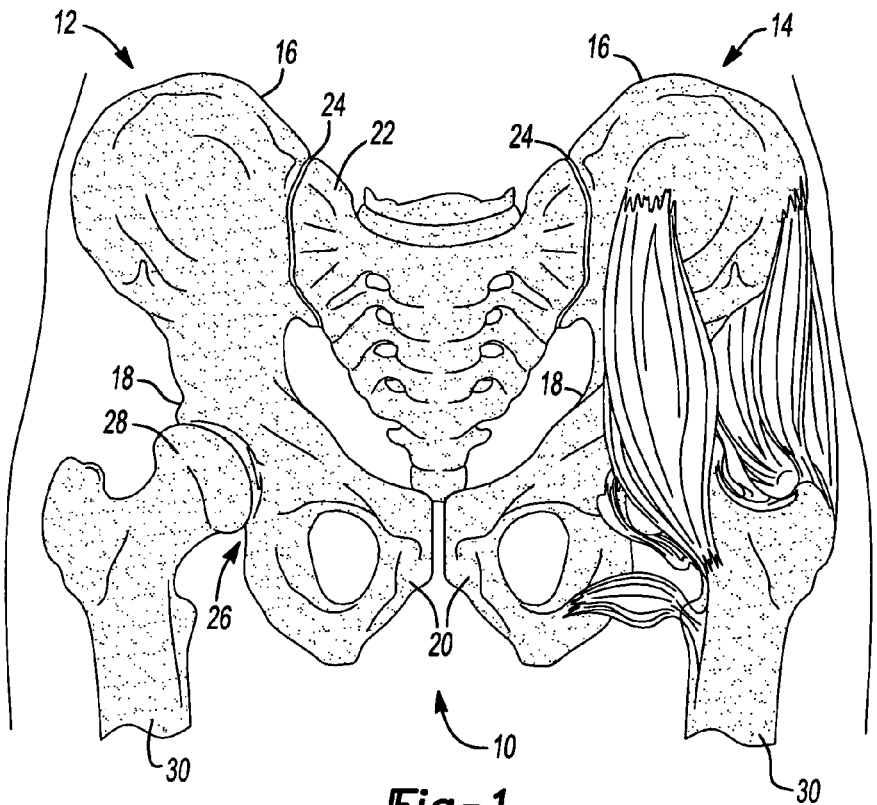
Fig-1
PRIOR ART
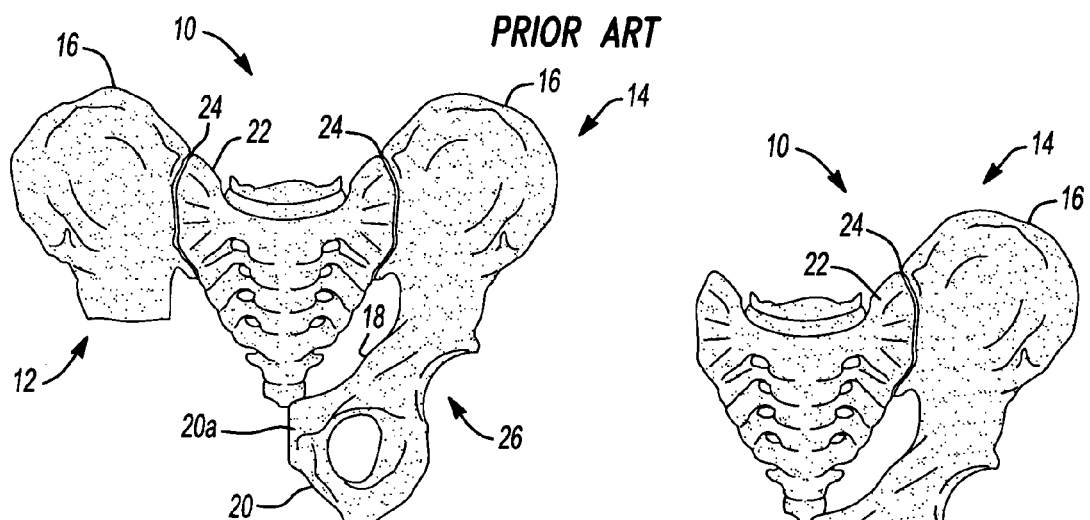
Fig-2
PRIOR ART
Fig-3
PRIOR ART

PUBIC CATCH

FIELD

The present invention relates to a hip bone prosthetic, and more particularly relates to a hip bone prosthetic that connects to the adjoining healthy pubis bone with a sliding clamping member.

BACKGROUND

With reference to FIG. 1, a human pelvis is shown and generally indicated by reference numeral 10. The human pelvis 10 is comprised of a right and a left hemi-pelvis respectively indicated by reference numerals 12 and 14. The right and left hemi-pelvis 12 and 14 may also be referred to as a right and left hip bone 12 and 14, respectively. Mature hip bones 12 and 14 are each comprised of three principle bones fused together: An ilium 16, an ischium 18 and a pubis 20. The ilium 16 is the upper and the largest part of the pelvis and articulates on its inner aspect with a sacrum 22 at a sacroiliac joint 24. The ischium 18 is the more distal and posterior of the three principal bones of the pelvis 10 and may be commonly referred as a seat bone or a huckle bone. The pubis 20 is the more medial and anterior of the three principal bones of the pelvis 10 and may be commonly referred to as a share bone or a pubic bone.

The ilium 16, the ischium 18, and the pubis 20 are separated from each other by cartilage in young subjects (not shown) but are fused together as solid bone in a mature adult. The union of the ilium 16, the ischium 18, and the pubis 20 takes place, among other places, in and around a large cup-shaped articular cavity known as the acetabulum generally indicated by reference numeral 26. The acetabulum 26 is a hollow, cuplike portion of the hip bone 12 into which a head 28 of a femur 30 fits. The bone and muscle structure surrounding the head 28 of the femur 30 and the acetabulum 26 of the hip bone 12 allows for among other things the ability to walk. It will be appreciated that there are muscles and associated connective tissue that retain the head 28 of the femur 30 within the acetabulum 26 and also provide for flexing and motion of the femur 30 relative to the hip bone 12. It will also be appreciated that while reference is made to either the hip bone 12, the discussion hitherto and throughout is applicable to hip bone 14.

The sacrum 22 is a triangular-shaped bone lying between the fifth lumbar vertebra (partially shown) and the coccyx (partially shown), which can be commonly referred to as the tailbone. The sacrum 22 consists of five vertebrae fused together and it articulates on each side with the respective ilia 16 to form sacroiliac joints 24. The sacrum 22, as well of as the other bones of the pelvis 10, may become damaged due to injury, or various medical conditions such as cancer, osteoporosis or various medical trauma, and as such may have to be partially removed and/or replaced in whole.

With reference to FIG. 2, the various medical conditions as mentioned above may deprive a patient of the acetabulum 26 of the hip bone 12 thereby necessitating a prosthetic to be implanted in its place. It will be appreciated that damage to the hip bone 12 can range from loss of use of one of the acetabulums 26 all the way to complete loss of one or both of the hip bones 12 and 14. If presented with a complete loss of one of the hip bone 12, it will be appreciated that a prosthetic hip bone or hemi-pelvis must be constructed to not only connect to the head 28 of the femur 30 but also connect to the opposing pubis bone 20a and the sacrum 22. If the hip bone 12 is not a complete loss it will be appreciated that the hip bone replacement must connect to the remaining portions of the hip bone 12 to otherwise restore complete functionality to the pelvis 10.

Hip prosthetics require bone screws and/or bone fusing material to establish a suitable connection to the remaining and healthy portions of the hip bone. Hip prosthetics also require bolts or bone screws threaded through brackets to connect to the remaining healthy bone. The additional hardware adds cost and complexity. The brackets further require that a larger area of the remaining healthy bone be exposed.

SUMMARY

The various embodiments of the present invention include a prosthetic device for replacement of a hip bone. The prosthetic device includes an acetabular component configured to connect to a femoral implant and a pubis member. The pubis member connects to the acetabular component and includes a clamping portion that is configured to attach to an opposed healthy pubis bone. The pubis member further includes a worm drive that is configured to tighten the clamping portion against the opposed healthy pubis bone.

Further areas of applicability of the present invention will become apparent from the detailed description provided hereinafter. It should be understood that the detailed description and specific examples, while indicating the various embodiments of the present invention, are intended for purposes of illustration only and are not intended to limit the scope of the invention.

BRIEF DESCRIPTION OF THE DRAWINGS

The present invention will become more fully understood from the detailed description, the appended claims, and the accompanying drawings, wherein:

FIG. 1 is a partial front view of a human pelvis that includes two opposed hip bones each having an ilium, an ischium, and a pubis fused together to form an acetabulum, the acetabulum accepts a head of a femur;

FIG. 2 is a partial front view of the human pelvis of FIG. 1 showing one of the hip bones partially resected;

FIG. 3 is a partial front view of the human pelvis of FIG. 1 showing one of the hip bones completely resected;

DETAILED DESCRIPTION OF THE VARIOUS EMBODIMENTS

The following description of the various embodiments is merely exemplary in nature and is in no way intended to limit the invention, its application, or uses. While the illustrated embodiments pertain to one hip bone or hip bone of the human body, it will be appreciated that the present invention is applicable to the bones of the pelvis of any creature and further is applicable to either the right or the left hip bone.

Figure 4:
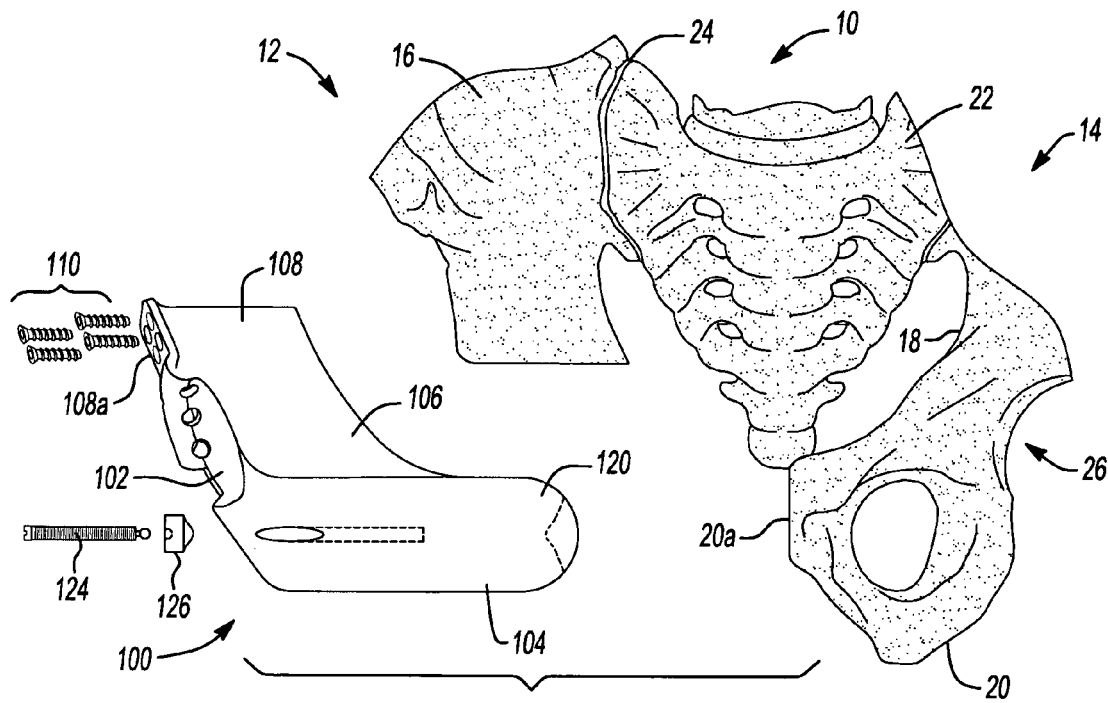
FIG. 4 is a partial front view of a pelvis showing a partial hip prosthetic constructed in accordance with the various embodiments of the present invention.
Figure 5:
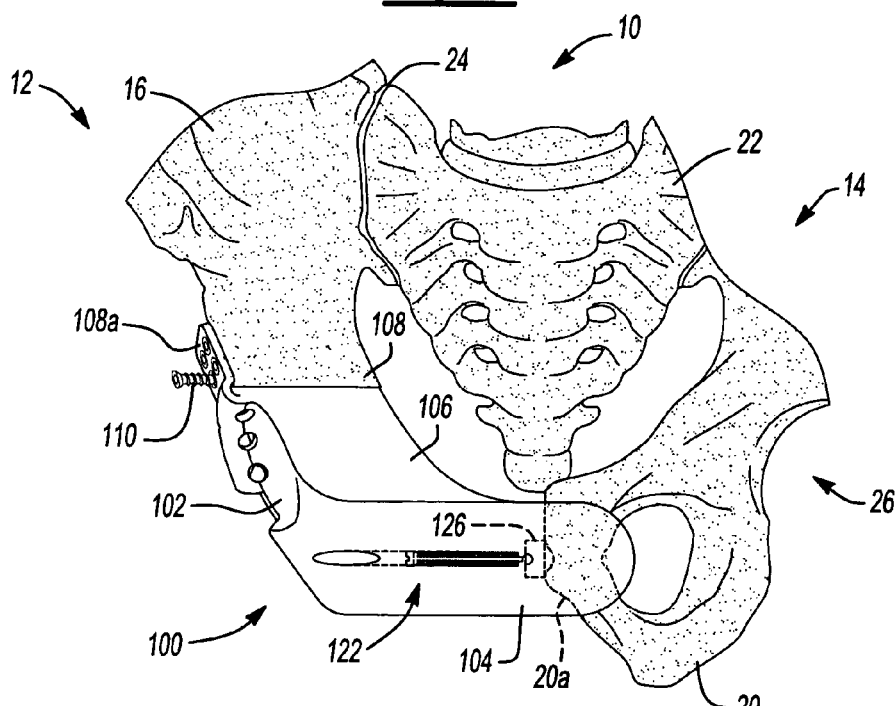
FIG. 5 is a partial front view of the pelvis showing the partial hip prosthetic of FIG. 4 connected to remaining healthy portions of the pelvis.
Figure 6:
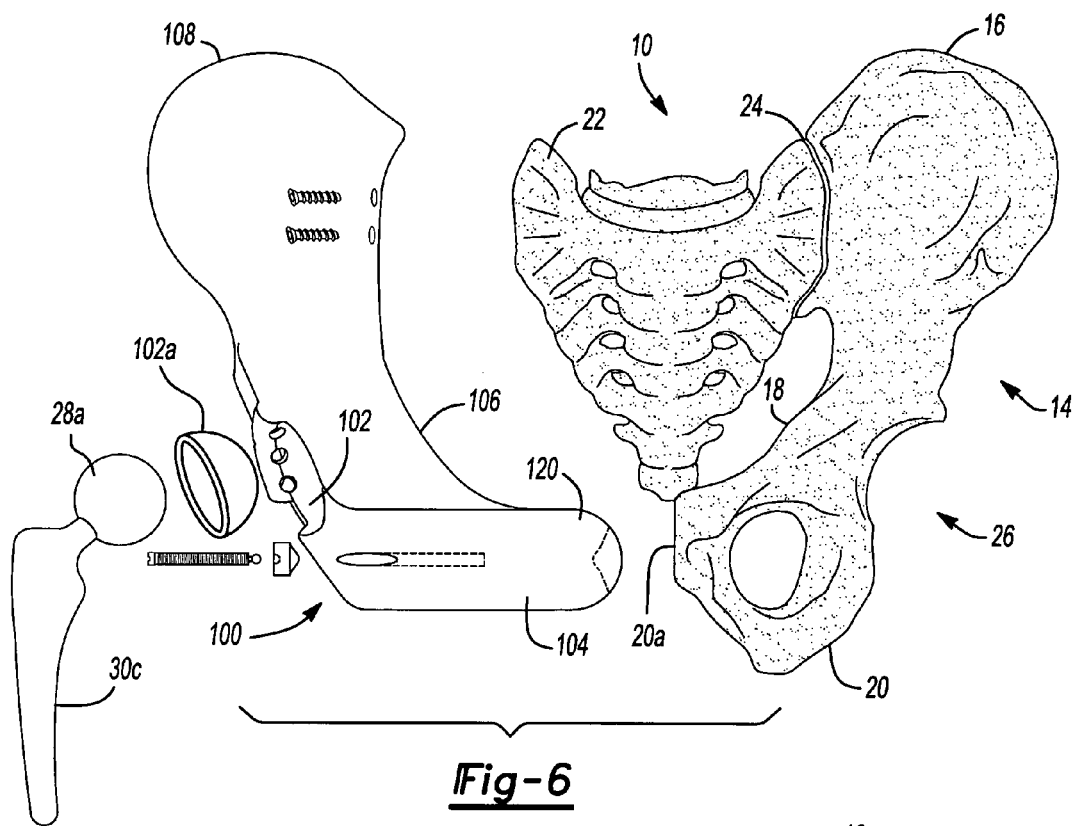
FIG. 6 is a partial front view of the pelvis showing a complete hip bone prosthetic replacement with a acetabular liner and a femoral component constructed in accordance with the various embodiments of the present invention.
Figure 10:
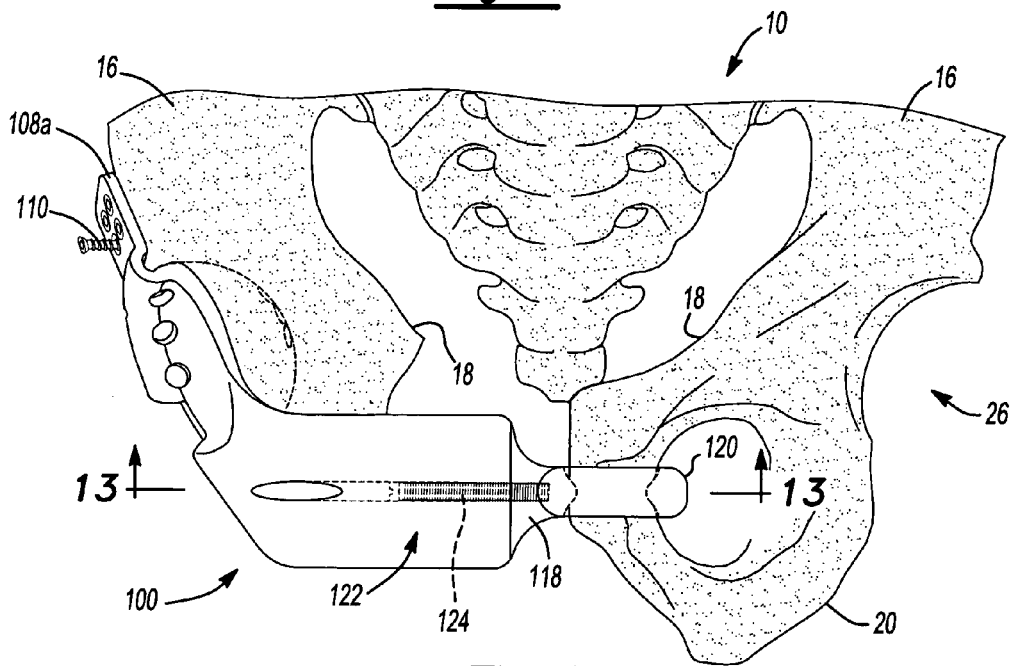
FIG. 10 is a partial front view of the pelvis showing the partial hip prosthetic of FIG. 9 connected to the remaining healthy portions of the healthy pelvis.

With reference to FIGS. 4-10, a hip prosthetic is generally indicated by reference numeral 100. In the various embodiments, the hip prosthetic 100 replaces all of or a portion of one of the hip bone's 12 of the pelvis 10. The hip prosthetic 100 includes an acetabular component 102 connected with a pubis member 104, an ischium member 106, and an ilium member 108. It will be appreciated that as more of a damaged hip bone 12 is removed due to various medical concerns, the replacement hip prosthetic 100 can be sized accordingly to otherwise replace a completely removed hip bone 12, as shown in FIG. 6. In FIGS. 5 and 10, for example, portions of the hip bone 12 remain after resection so that the hip prosthetic 100 is sized to connect to remaining and healthy portions of the hip bone 12. It will be appreciated portions of the hip bone prosthetic or connectors used therewith can be sized and configured accordingly to produce a kit of modular of components.

The acetabular component 102 is configured to mimic the acetabulum 26 of a healthy hip bone 12, as shown in FIG. 1. Similar to one of the hip bone 12, the acetabular component 102 is formed around the interconnection of the pubis member 104, the ischium member 106 and the ilium member 108. In the various embodiments, the acetabular component 102 is sized to mate with a femoral component 30a that serves as, among other things, a prosthetic head 28a to the femur 30, as shown in FIG. 6. As such, the joint between the femur 30 and the hip bone 12 can be comprised of artificial components and/or one or more bushings or liners made of suitable metals, plastics or ceramics.

The acetabular component 102 can be configured as an acetabular cup to accept a prosthetic femoral head 28a of the femoral component 30a. It will be appreciated that the acetabular component 102 can also be configured to receive an acetabular cup, such that the acetabular cup can be positioned and seated in the acetabular component 102 and secured with suitable bone cement or other suitable fasteners. It will be additionally appreciated that additional liners 102a or bushings may be included in the acetabular component 102 to further facilitate the junction between the acetabular component 102 and the prosthetic femoral head 28a. More specifically, the prosthetic femoral head 28a can be attached to the acetabular component 102 using, for example, ring locks, or taper junctions. Furthermore, the acetabular component 102 can be configured to accept the natural femoral head 28. In this instance, additional liners 102a and/or bushing can be used to facilitate the junction between the acetabular component 102 and the natural femoral head 28.

Figure 11:
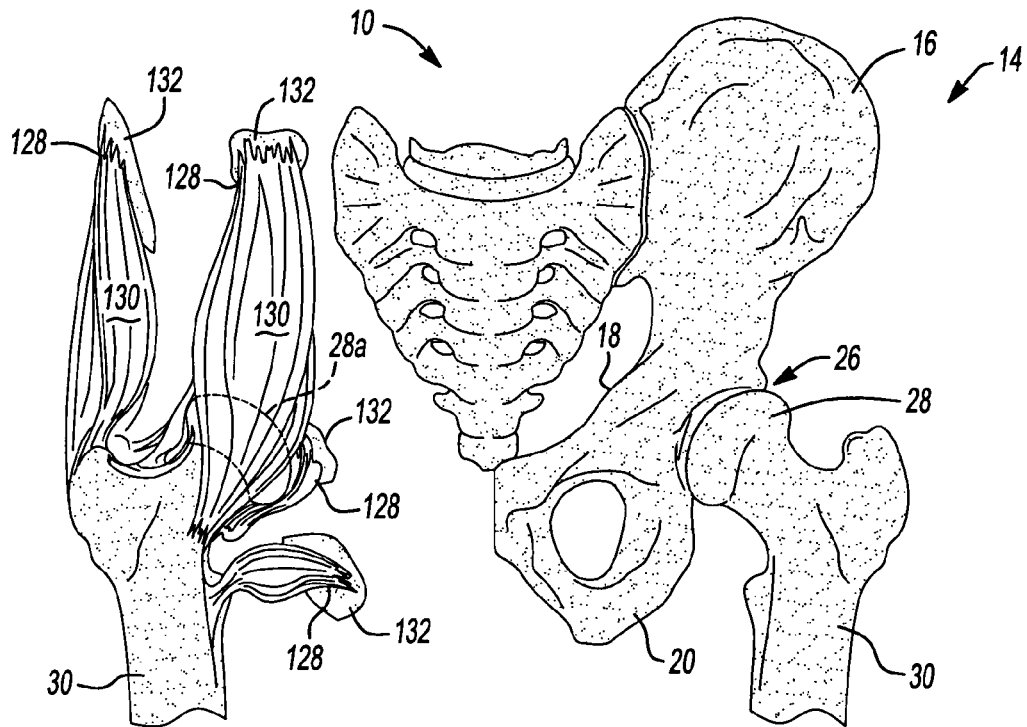
FIG. 11 is a partial front view of the pelvis with one of the hip bones partially resected leaving a plurality of bone portions attached to the associated connective tissue in preparation for reattachment of the plurality of bone portions to the prepared hip bone prosthetic.

The ilium member 108 and the ischium member 106 can be configured to otherwise mimic the natural configuration of the hip bone 12 (FIG. 1). More specifically, a patient receiving the hip prosthetic 100 can be examined before the hip replacement surgery so that the hip prosthetic 100 can be configured to be generally identical to the portions of the hip bone 12 that the hip prosthetic replaces. It will be appreciated that if the hip bone 12 is completely removed, as shown in FIG. 6, that the hip prosthetic 100 must connect directly to the sacrum 22 as opposed to connecting to the remaining healthy portions of the hip bone 12. It will also be appreciated that portions of the otherwise healthy ilium 16 or ischium 18 can be resected from the patient and attached to portions of the hip prosthetic 100 to further serve in expediting the rehabilitation process, as shown in FIG. 11. This process will be discussed in greater detail below.

Figure 7:
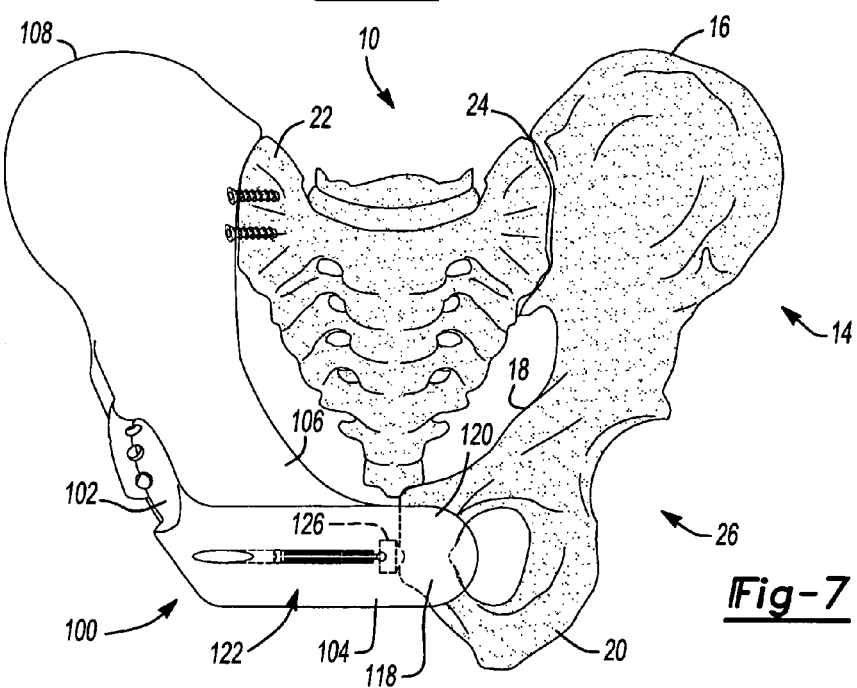
FIG. 7 is a partial front view of the pelvis showing the complete hip prosthetic of FIG. 6 connected to the remaining healthy portions of the pelvis.
Figure 8A:
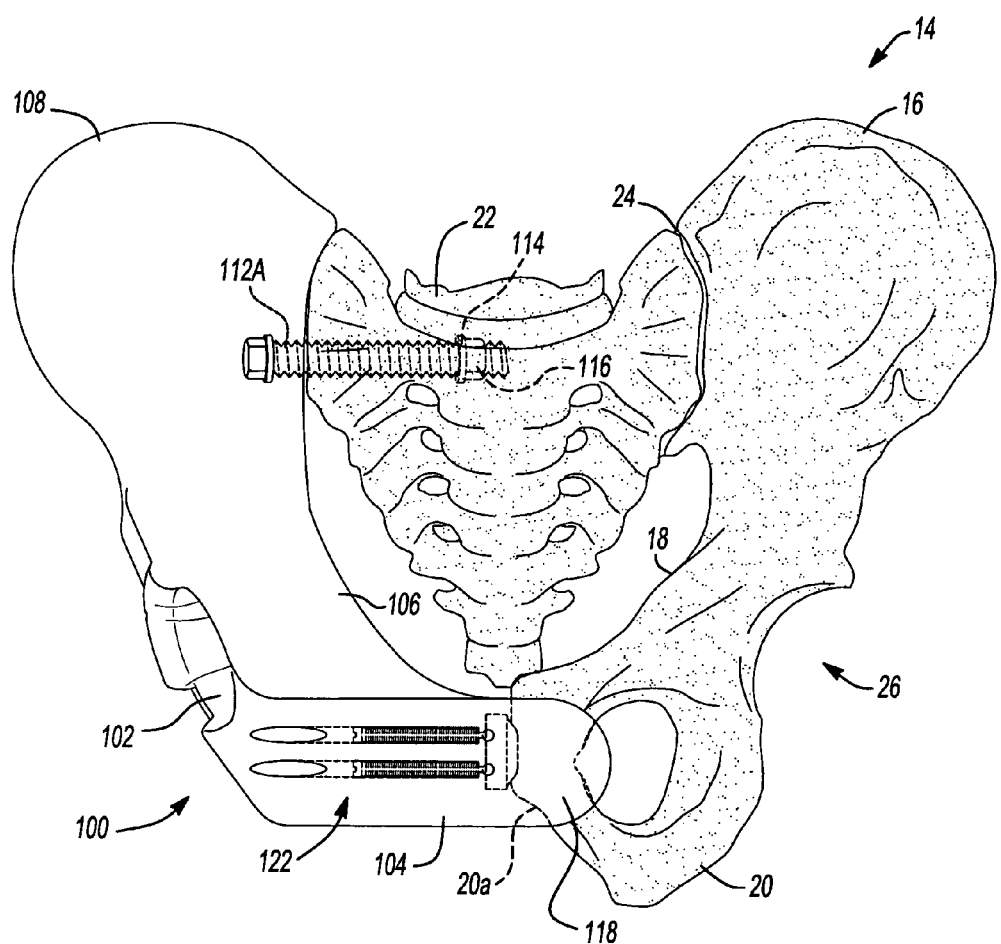
FIG. 8A is a partial front view of the pelvis showing the complete hip bone prosthetic replacement of FIG. 7 with an alternative fastener between the complete hip prosthetic and a sacrum and an alternative configuration of a worm drive constructed in accordance with the various embodiments of the present invention.
Figure 8B:
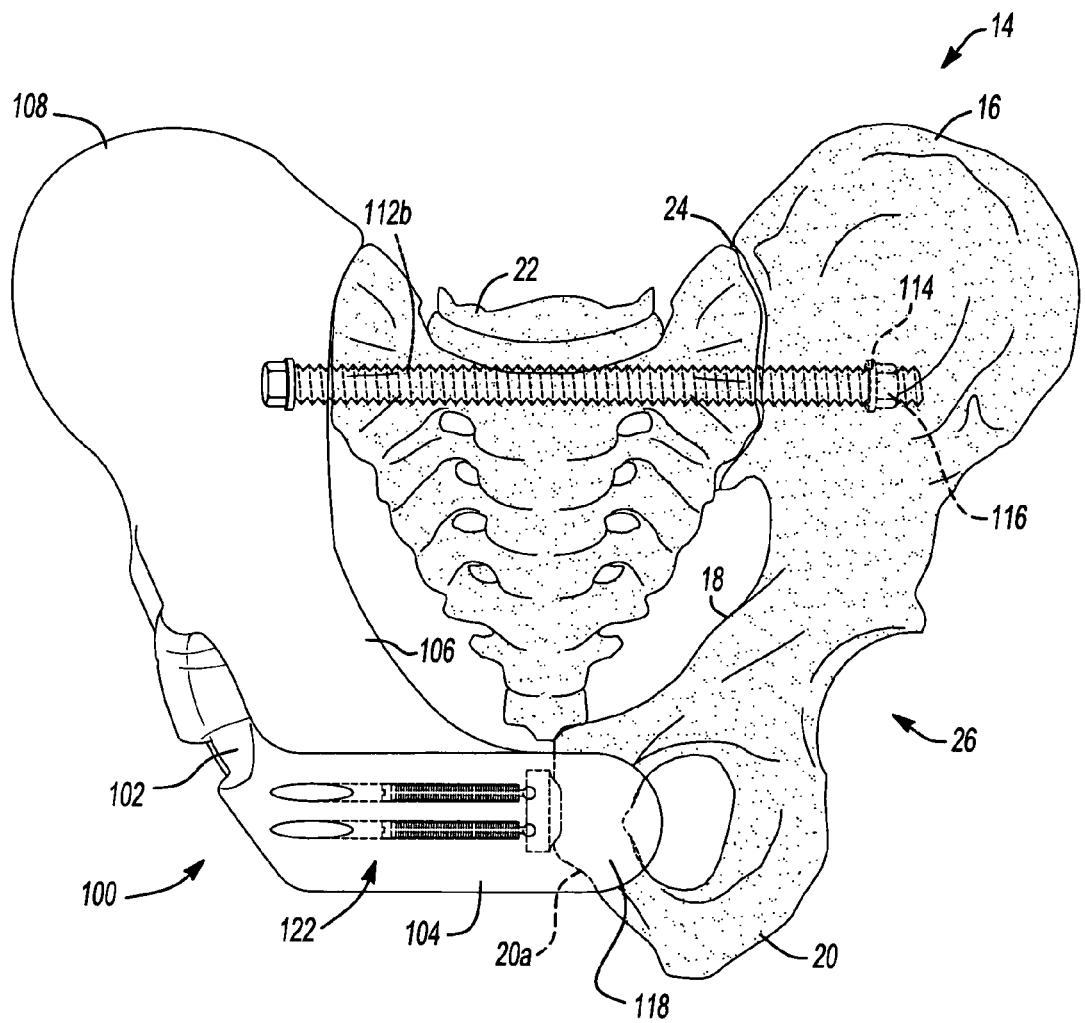
FIG. 8B is a partial front view of the pelvis showing the complete hip bone prosthetic replacement of FIG. 7 with an alternative fastener between the complete hip prosthetic, a sacrum, and the healthy hip bone.
Figure 9:
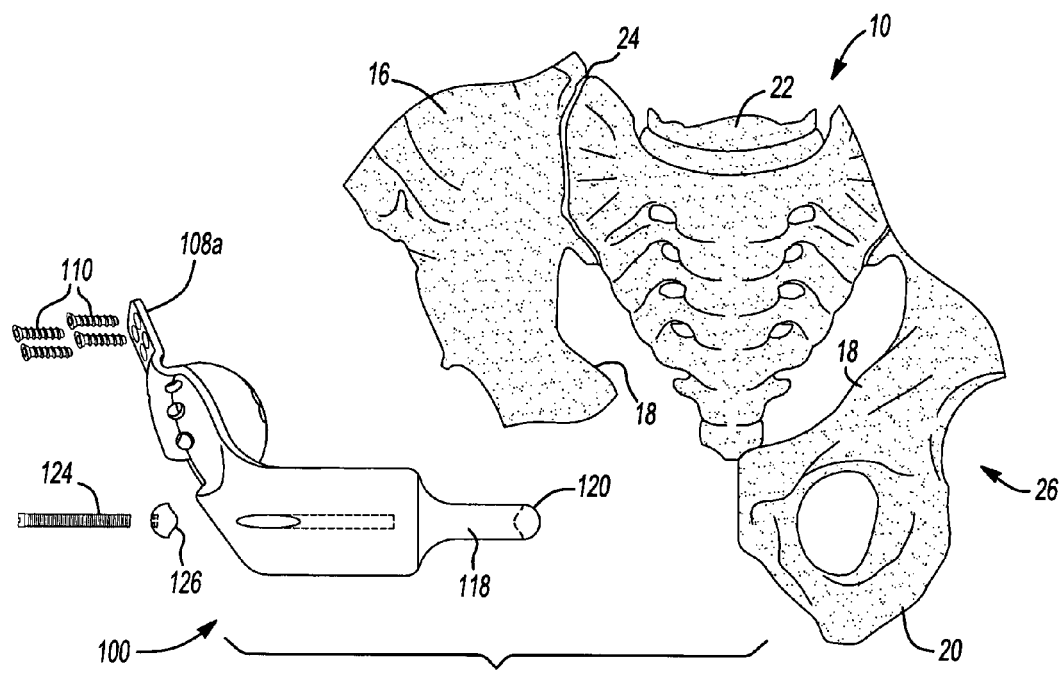
FIG. 9 is a partial front view of the pelvis showing an alternative partial hip prosthetic constructed in accordance with the various embodiments of the present invention.

If the hip bone 12 is completely removed and the hip prosthetic 100 must serve as essentially a new hip bone 12, the ilium member 108 of the hip prosthetic 100 can be configured to connect directly to the sacrum 22. Connection to the sacrum 22 can be accomplished by driving suitable bone screws 110 through portions of the ilium member 108 and through portions of the sacrum 22 to connect thereto, as shown in FIG. 7. In the various embodiments, a suitable bolt 112 can also be used such that one or more holes are drilled in the ilium member 108 and in the sacrum 22, as shown in FIG. 8A, and through the sacrum 22 into the opposed ilium member 16, as shown in FIG. 8B. A bolt 112A is passed through the ilium member 108 and into the sacrum 22 and is connected thereto with the washers 114 and fasteners 116, as shown in FIG. 8A. In FIG. 8B, a bolt 112B is passed through the ilium member 108 and the sacrum 22 to the healthy ilium 16 and is connected thereto with the washers 114 and fasteners 116, thereby pulling the ilium member 108 in close contact with the sacrum 22 and ilium 16.

In the various embodiments when the hip bone 12 is not completely removed, the ilium member 108 of the hip prosthetic 100 can be connected to the remaining healthy portion of the ilium 16. As shown in FIGS. 4 and 5, portions of the healthy hip bone 12 may remain while portions of the damaged bone are resected. In this case, the pubis member 104, the ilium member 108 and the ischium member 106 of the hip prosthetic 100 can be configured to connect to the remaining healthy portions of the otherwise healthy hip bone 12.

In the various embodiments, a connecting flange 108a can be configured to engage the remaining healthy portions of the hip bone 12. Bone screws 110 can be driven though the connecting flange 108a and into the hip bone 12 to secure the prosthetic hip 100. It will be appreciated that the connecting flange 108a can be connected to the ilium member 108 of the prosthetic hip 100 to engage the remaining portion of the ilium 16. The connecting flange 108a can also be located at other locations on the prosthetic hip 100 to facilitate connection to other portions of the pelvis 10 with bone screws 100 or other suitable fasteners such as bone cement or a porous material to promote bone growth into the connecting flange 108a.

The pubis member 104 of the hip prosthetic 100 is connected to the acetabular component 102 and also serves as a connection to the opposed healthy pubis bone 20a of the healthy hip bone 14. The pubis member 104 includes a connecting member 118 that connects the acetabular component 102 to a clamping portion 120. The clamping portion 120 includes a worm drive generally indicated by reference number 122. The worm drive 122 includes one or more threaded rods 124 that are attached to a catch plate 126 that is driven against the opposed pubis bone 20a of the opposite healthy hip bone 14. When the catch plate 126 is driven against the pubis bone 20a, the clamping portion 120 is drawn from the side opposite the catch plate 126 thereby clamping the opposed pubis bone 20a between the catch plate 126 and the clamping portion 120.

Figure 14:
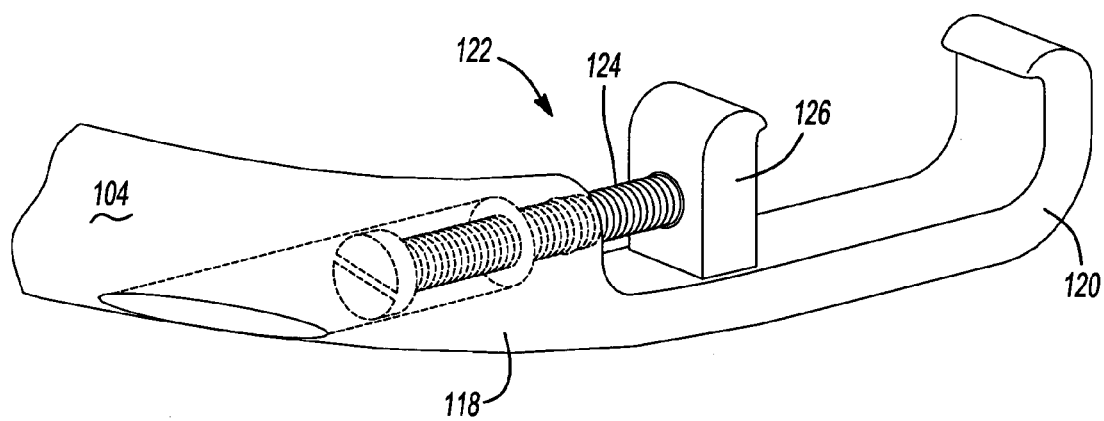
FIG. 14 is a partial perspective view of FIG. 13 showing the pubis member including the worm drive, a catch plate and the clamping portion.
Figure 16:
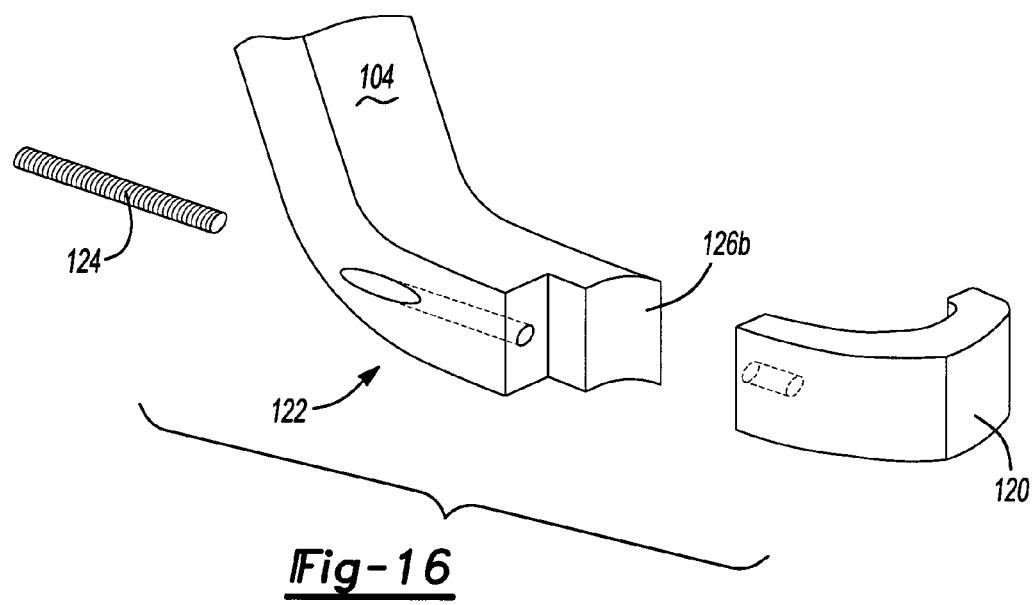
FIG. 16 is a partial perspective view of the pubis member configured with an alternative clamping portion constructed in accordance with the various embodiments of the present invention.

The worm drive 122 of the clamping portion 120 is configured with the pubis member 104 so that the clamping portion 120 can simply be tightened by rotating the worm drive 122. Various configurations of the catch plate 126, as shown in FIGS. 14 and 16, and multiple worm drives 122, as shown in FIG. 8, can be used to further connect and stabilize the clamping portion 120 to the opposed hip bone 14. It will further be appreciated that multiple catch plates 126 and various configurations of the clamping portion 120 can be used and that each of the catch plates 126 can be further configured to compliment the shape of the opposed pubis bone 20a to which it contacts. It will additionally be appreciated that multiple worm drives 122 can be used with a single catch plate 126 or multiple catch plates 126 to further facilitate connection to the pubis bone 20a.

Figure 15:
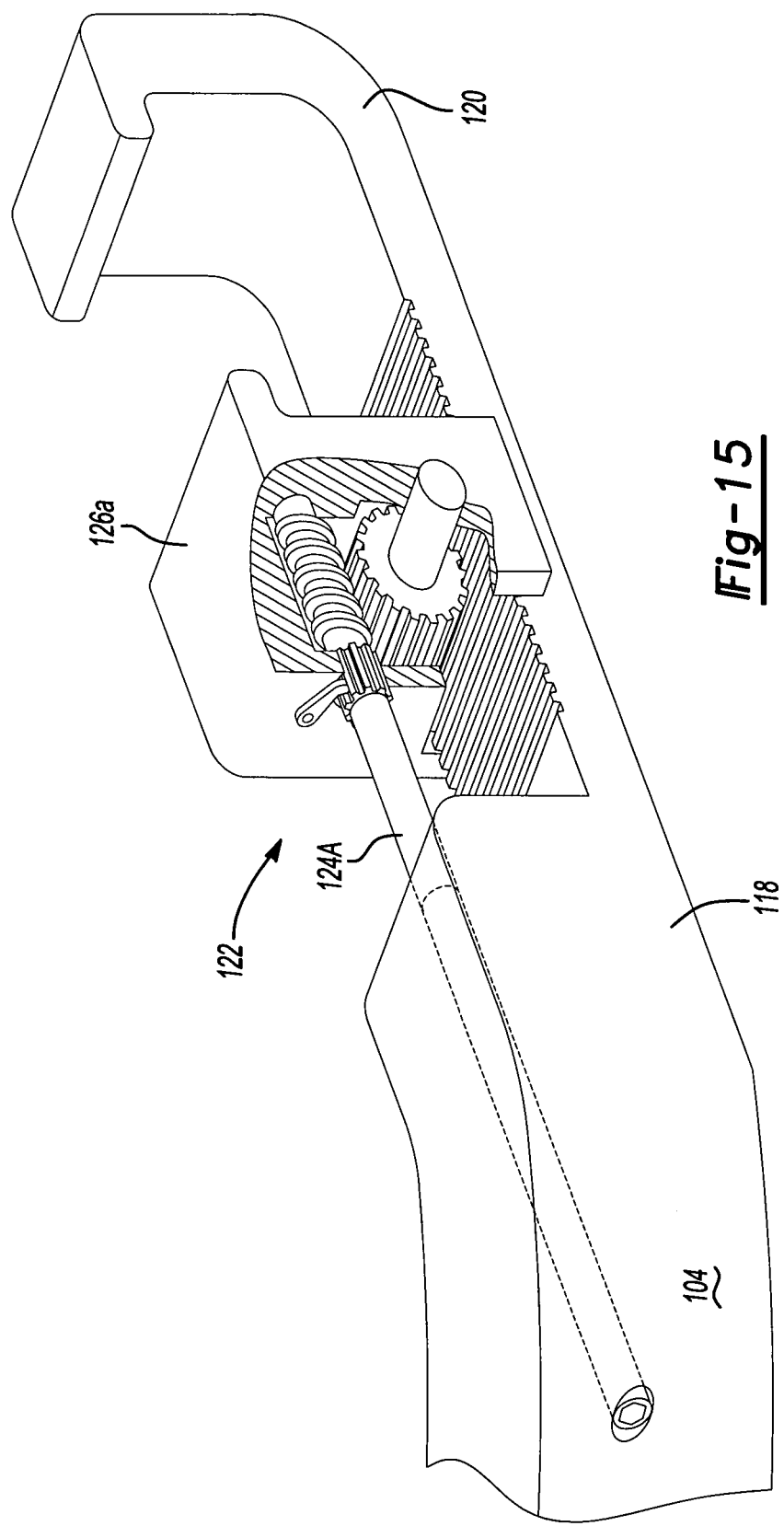
FIG. 15 is a partial perspective view of the pubis member configured with an alternative clamping portion having a ratcheting worm drive constructed in accordance with the various embodiments of the present invention.

With specific reference to FIG. 15, the clamping portion 120 and catch plate 126 can be configured so the at the catch plate ratchets and slides toward the clamping portion 120. Rotation of a partially threaded rod 124a drives the catch plate 126. A catch plate ratchet 126a can be configured to ratchet closed and open by releasing the ratchet. The opposite is also possible.

With specific reference to FIG. 16, the clamping portion 120 can be configured so that the catch plate 126b is fixed and the clamping portion 120 is drawn toward the pubis member 104 when the worm drive 122 is rotated. The catch plate 126b can be configured as an integral portion or movably connected thereto. In the various embodiments, the clamping portion 120 can be a single clamp or be configured with multiple clamping portions 120 driven by multiple worm drives 122. Further, a single clamping portion 120 may be driven by multiple worm drives 122 to further facilitate stabilization of the pubis member 104.

Figure 17:
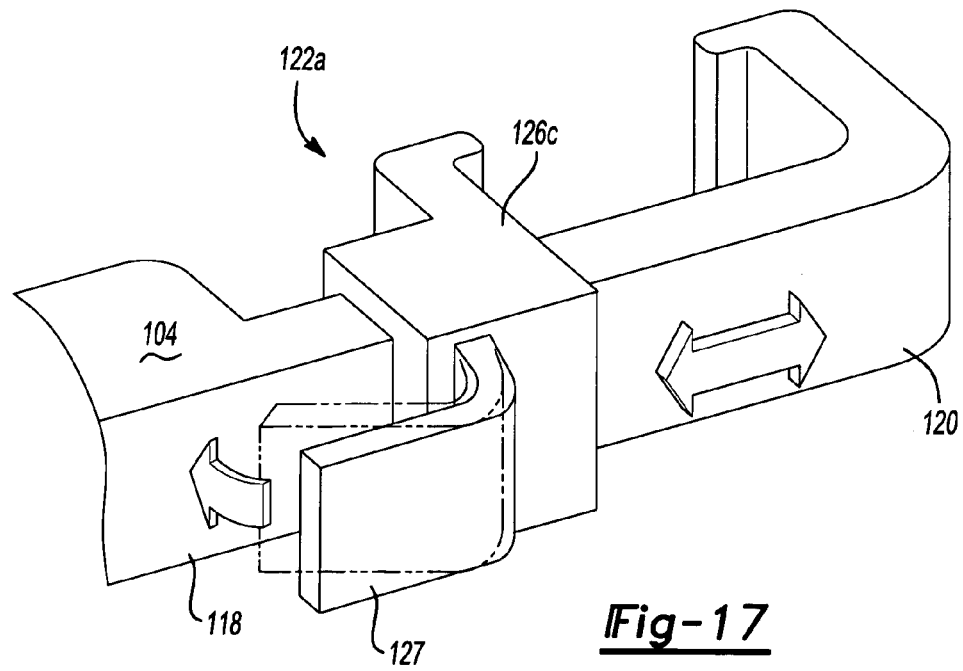
FIG. 17 is a partial perspective view of the pubis member configured with an alternative clamping portion having a spring lever constructed in accordance with the various embodiments of the present invention.

With specific reference to FIG. 17, the clamping portion 120 can be configured so that the catch plate 126c contains a spring clamp 127. The catch plate 126c is advanced toward or can retreat from the clamping portion 120 when the spring clamp 127 is released. In the various embodiments, the clamping portion 120 can be a single clamp or be configured with multiple clamping portions 120.

Figures 18, 19:
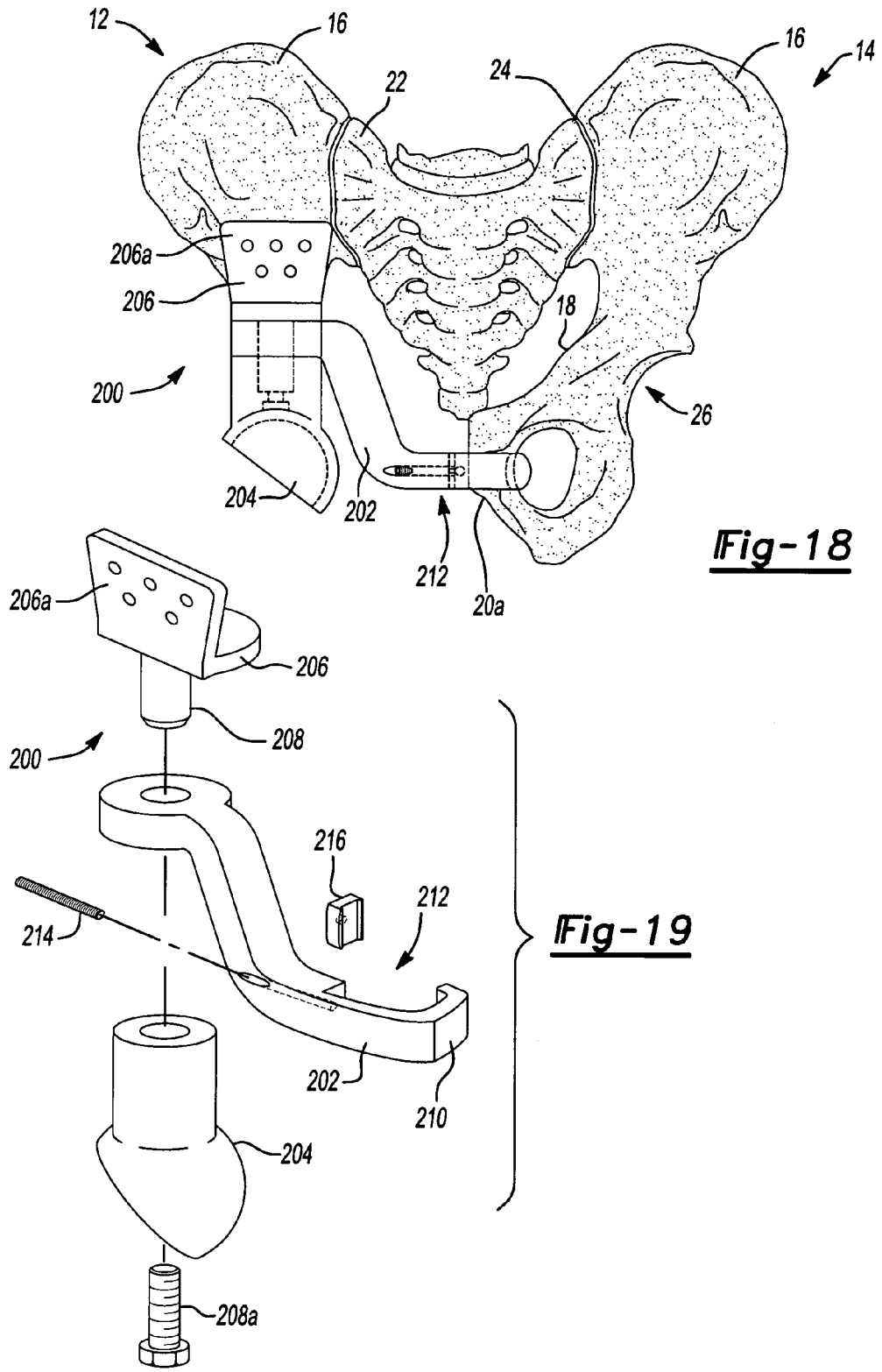
FIG. 18 is a front view of the pelvis showing an alternative configuration of the partial hip prosthetic with modular components including a pubic clamp component, a hip flange component, and a acetabular component constructed in accordance with the various embodiments of the present invention.
FIG. 19 is an exploded perspective view of the partial hip prosthetic of FIG. 16 showing the public clamp component including a worm drive and a clamping portion.

With reference to FIGS. 18 and 19, the hip prosthetic 100 can also be made of a modular multi-component construction generally indicated by reference numeral 200. The modular prosthetic hip 200 includes a pubis clamp component 202, an acetabular component 204, and a hip flange component 206. The hip flange component 206 includes an assembly rod 208 that is inserted through the pubis clamp component 202 through to the acetabular component 204 and held together with an assembly rod fastener 208a. Because the pubis clamp component 202 is inserted over the assembly rod 208 it can move relative to the acetabular component 204. It will also be appreciated that the various components of the modular prosthetic hip 200 can be passed into the surgical area piece by piece and assembled in the surgical area, thus providing a less invasive technique.

In the various embodiments, a connecting flange 206a can be configured to engage the remaining healthy portions of the hip bone or hip bone 12. Bone screws 110 (FIG. 9) can be driven though the connecting flange 206a and into the hip bone 12 to secure the modular prosthetic hip 200. It will be appreciated that the connecting flange 206a can be connected to the hip flange component 206 in various positions and locations to engage the remaining portion of the ilium 16 or other portions of the pelvis 10. The connecting flange 206a can also be configured in a cup-like bow-like fashion to further facilitate connection of the modular prosthetic hip 200 to other portions of the pelvis 10. The connecting flange 206a can be connected to portions of the pelvis with bone screws 100 or other suitable fasteners such as bone cement or a porous material to promote bone growth into the connecting flange 108a.

The acetabular component 204 can be configured as an acetabular cup to accept a prosthetic femoral head 28a of the femoral component 30a (FIG. 6). It will be appreciated that the acetabular component 204 can be configured to receive an acetabular cup, such that the acetabular cup can be positioned and seated in the acetabular component 204 and secured with suitable bone cement or other suitable fasteners. It will be additionally appreciated that additional liners 102a (FIG. 6) or bushings may be included in the acetabular component 204 to further facilitate the junction between the acetabular component 204 and the prosthetic femoral head 28a. More specifically, the prosthetic femoral head 28a can be attached to the acetabular component 204 using, for example, ring locks, or taper junctions. Furthermore, the acetabular component 204 can be configured to accept the natural femoral head 28. In this instance, additional liners 102a and/or bushing can be used to facilitate the junction between the acetabular component 204 and the natural femoral head 28.

A clamping portion 210 of the pubis clamp component 202 is similar to that of the clamping portion 120, as shown in FIG. 14. As such, the pubis clamp component 202 includes a worm drive generally indicated by reference numeral 212. The worm drive 212 includes a threaded rod 214 threaded through the pubis clamp component 202. The threaded rod 214 connects to a catch plate 216. Rotating the worm drive 212 tightens the catch plate 216 against the pubis bone 20a and draws the pubis clamp component 202 closer to the catch plate 216, thus securing the pubis bone 20a in the pubis clamp component 202.

The worm drive 212 can also be configured such that one or more of the threaded rods 214 are attached to one or more of the catch plates 216, which further facilitate holding the pubis bone 20a in the pubis clamp component 202. It will be appreciated that various sizes of the catch plates 216 and the multiple worm drives 212, as illustrated in FIG. 8, can be used to further connect and stabilize the pubis clamping component 202 to the opposed pubis bone 20a. It will further be appreciated that the catch plates 216 can be further configured to compliment the shape of the opposed pubis bone 20a. It will be additionally appreciated that multiple worm drives 212 can be used with a single catch plate 216 or multiple catch plates 216 to further facilitate connection to the pubis bone 20a.

It will also be appreciated, that the pubis clamp component 202 can be configured so that the catch plate 216 is fixed and the clamping portion 210 is drawn toward the assembly rod 208 when the worm drive 212 is rotated, similar to that of FIG. 15. The fixed catch plate 216 is configured as an integral portion of the pubis clamp component 202 and the clamping portion 210 is attached to worm drive 212, such that the clamping portion 120 can be driven away from or toward the assembly rod 208 upon rotation of the worm drive 212. As with other various embodiments of the present invention, the clamping portion 210 can be a single clamp or be configured with multiple clamping portions 210 driven by multiple worm drives 212. Further, a single clamping portion 210 may be driven by multiple worm drives 212 to further facilitate stabilization of the pubis clamp component 202. In addition, the clamping portion 210 and the catch plate can be configured with the functionality from the catch plate ratchet 216 (FIG. 15) and the spring lever 127 (FIG. 17).

Figure 20:
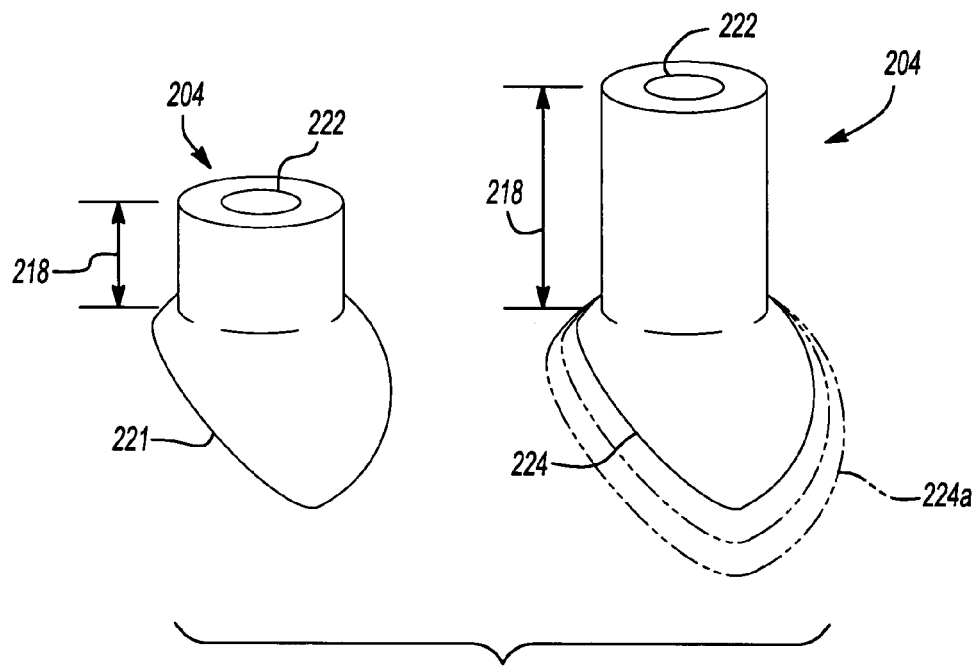
FIG. 20 is a perspective view of the acetabular component of FIG. 16 illustrating various configurations of the acetabular component constructed in accordance with the various embodiments of the present invention.
Figure 21:
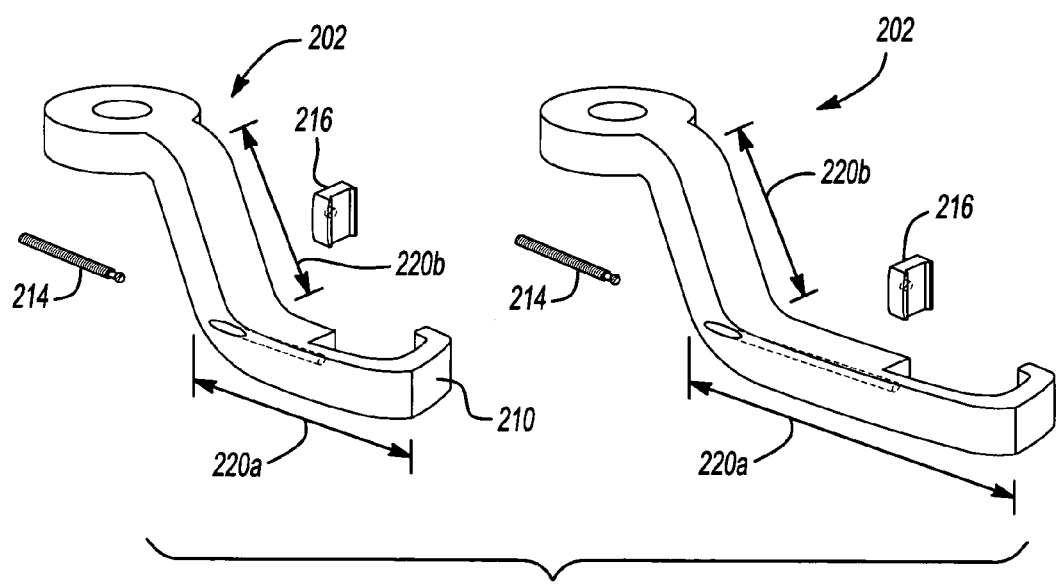
FIG. 21 is a perspective view of the acetabular component of FIG. 16 illustrating various configurations of the pubic clamp component constructed in accordance with the various embodiments of the present invention.
Figure 22:
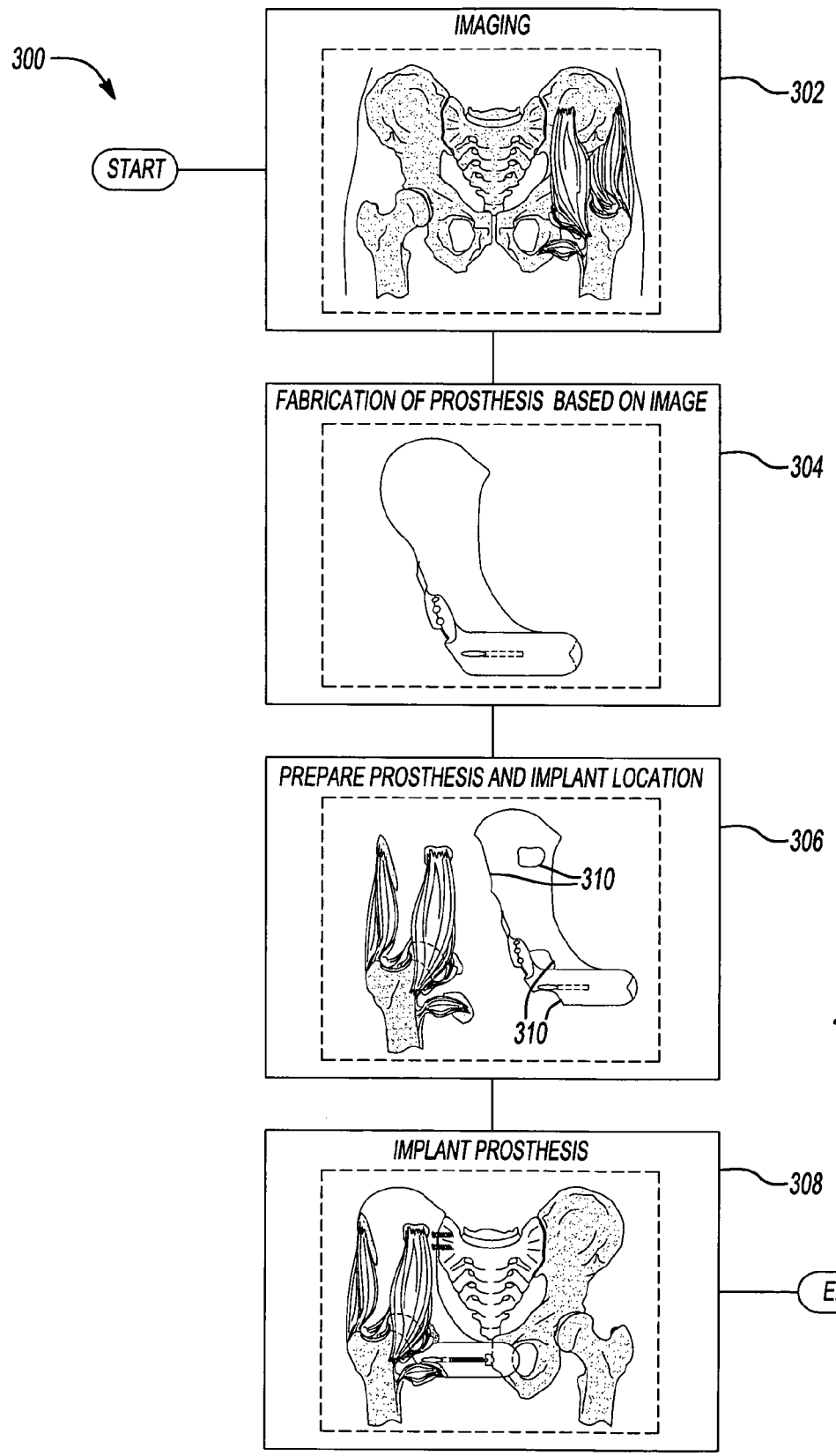
FIG. 22 is a flowchart illustrating the method of fabricating and implanting the hip prosthetic based on imaging of portions of the healthy pelvis.

With reference to FIGS. 20 and 21, it will be appreciated that the various components of the modular prosthetic hip 200 can be sized based on the size of the remaining portions of the pelvis 10 (FIG. 1) and other restrictions that can exist in the operating area. As such, the acetabular component 204 can be configured in different sizes, all of which can be available to the doctor during surgery. An acetabular neck length 218 and clamping portion lengths 220a and 220b can vary based on, among other things, the patient's anatomy. It will be appreciated that an aperture 222 on the acetabular component can also be recessed further in the acetabular component 204 to adjust positioning and length. For example, the female pelvis is smaller than the male pelvis, and furthermore the pelvis of a child is smaller than that of an adult. Because of the varying sizes required, the modular prosthetic hip 200 can be provided in many different sizes. The modular prosthetic hip 200 can also be configured to connect to a prosthetic femoral component, and as such, an acetabular cup 224 can be fabricated in various sizes 224a to fit the various modular femoral components available.

Figure 12:
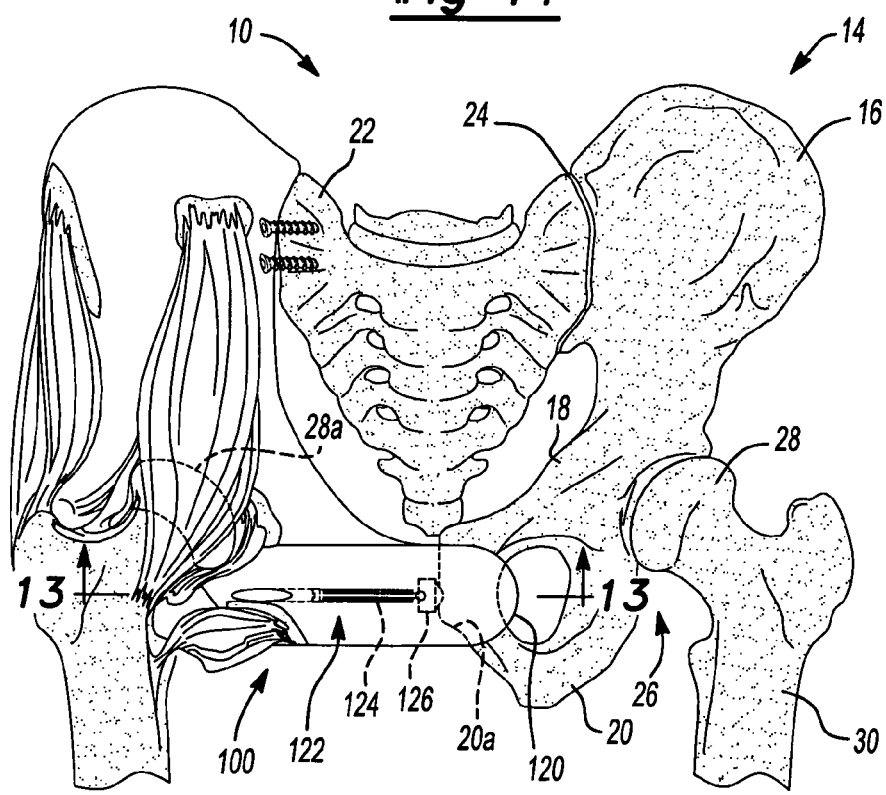
FIG. 12 is a partial front view of the pelvis of FIG. 11 showing the complete hip prosthetic connected to the plurality of bone portions attached to the associated connective tissue and also secured to the sacrum and the opposed healthy pubis bone.
Figure 13:
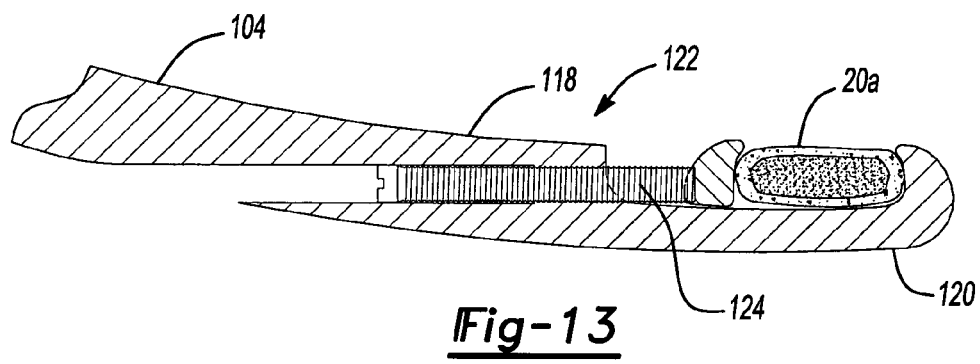
FIG. 13 is a cross section view from FIGS. 10 and 12 showing a pubis member of the hip prosthetic having a clamping portion and the worm drive that clamps the opposed healthy pubis bone to the pubis member of the hip prosthetic replacement constructed in accordance with the teachings of the present invention.

With reference to FIGS. 1, 12, and 20, a method of using the hip prosthetic 100 is generally indicated by reference numeral 300. In block 302, a patient's healthy pelvis is imaged by a suitable imaging system to produce three-dimensional information of the patient's healthy pelvis. An exemplary suitable imaging machine can be, but is not limited to, a computed tomography (CT) imaging system or a Computed Axial Tomography (CAT) imaging system. It will be appreciated that the three dimensional data may be obtained either from the pelvis 10 or specifically from the hip bone 12, which is the hip bone that is to be replaced.

In some instances, however, the hip bone 12 may be so damaged for various reasons such that imaging of the hip bone 12 would be impractical. In this instance, the three-dimensional information can be obtained from the remaining healthy portions of the pelvis 10 and specifically from the opposed healthy hip bone 14. If the hip bone 14 is imaged to obtain three-dimensional information for the fabrication of the hip prosthetic 100, which will replace the hip bone 12, the three-dimensional information can be converted so that it can be used to re-create the prosthetic version of the hip bone 12. As stated earlier, it will be appreciated that replacement of the hip bone 12 is for illustration purposes only and the present invention is applicable to the replacement of the hip bone 14 and to the pelvis 10. From block 302, the method 300, proceeds to block 304.

In block 304, the three-dimensional information, obtained in block 302, is used to fabricate the hip prosthetic 100. It will be appreciated that there are many ways to fabricate the hip 100, such various rapid prototyping systems known to one skilled in the art. Furthermore, the three-dimensional information can be converted to computer-numerical-control (CNC) code can be used in CNC machines. Whichever manufacturing process is used, the hip prosthetic must be made of material that is suitable for implantation into the body and is durable enough for that same purpose. Exemplary materials include, but are not limited to, cobalt chrome, titanium or suitable polymers used for in vivo prosthetics, and known to one skilled in the art. From block 304, the method 300, proceeds to block 306.

In block 306, the prosthetic 100 is prepared along with the area around the healthy hip for receipt of the prosthetic 100. When the hip bone 12, or portions thereof, is resected from the pelvis 10 in preparation for replacement with the hip prosthetic 100, the plurality of bone portions 132 (FIG. 11) connected to the respective connective tissue 128 (FIG. 11) can be left behind to aid re-connection to the hip prosthetic 100. Likewise, portions of the hip prosthetic 100 can also be configured with a plurality of anatomical connection points 310 to mate with the plurality of bone portions 132. This procedure avoids connecting the connective tissue 128 directly to the hip prosthetic 100. It will be appreciated that the anatomical connection points 310 can also be configured as apertures, such that the boney portion 132 can be passed through and attached thereto. After block 306, the method 300 proceeds to block 308.

In block 308, the prosthesis can be implanted and attached to the pelvis 100. The plurality of the bone portions 132 can be attached to the plurality of the anatomical connection points 310. If the hip prosthetic 100 serves as a complete replacement to the hip bone 12, the hip prosthetic 100 can be attached to the sacrum 22, as shown in FIG. 7. If the hip prosthetic 100 serves as a partial replacement to the hip bone 12, the hip prosthetic 100 can be attached to the remaining portions of the hip bone 12, as shown in FIG. 5. Nevertheless, the hip prosthetic 100 is attached to either the sacrum 22 or the remaining portions of the hip bone 12 with the bone screws 110 (FIG. 9) or other suitable fasteners or bonding materials. The pubis member 104 can be attached to the opposed healthy pubis bone 20a. The worm drive 122 can then be tightened to clamp the clamping portion 120 over the opposed healthy pubis bone 20a and secure the hip prosthetic 100.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A prosthetic device for replacement of at least an acetabulum of a first hemi-pelvis of a pelvis of a patient that defines a sagittal plane through the pelvis so a second hemi-pelvis is on a side of the sagittal plane opposite the first hemi-pelvis, the prosthetic device comprising:
   an acetabular component operable to replace at least the acetabulum of the first hemi-pelvis; and
   a pubis member connected to said acetabular component, said pubis member including a clamping portion and a catch plate that is moveable relative to the clamping portion, said clamping portion and said catch plate operable to attach to an opposed pubis bone of the second hemi-pelvis on the side of the sagittal plane that is opposite said acetabular component by holding said opposed pubis bone between said catch plate and said clamping portion.

2. The prosthetic device of claim 1, wherein said clamping portion includes a worm drive that advances said catch plate toward said clamping portion of said pubis member with rotation of a threaded rod.

3. The prosthetic device of claim 2, wherein said clamping portion extends a length to enable said catch plate and said clamping portion to fixedly connect said pubis member of the prosthetic device to the opposed pubis bone of the second hemi-pelvis of the pelvis.

4. The prosthetic device of claim 1, wherein said acetabular component is adapted to connect to a femoral implant.

5. The prosthetic device of claim 4 wherein the prosthetic device includes an ilium member and an ischium member connected to said acetabular component and operable to at least partially replace the first hemi-pelvis.

6. The prosthetic device of claim 5, wherein said ilium member is configured to connect to a remaining portion of a healthy ilium of the first hemi-pelvis with at least one of bone screws, threaded fasteners and bone cement.

7. The prosthetic device of claim 5, wherein said ilium member is configured to connect to a sacrum with at least one of bone screws, threaded fasteners and bone cement.

8. The prosthetic device of claim 1, further comprising a plurality of anatomical connections points formed on at least one of said pubis member, an ilium member and an ischium member, wherein said plurality of anatomical connections points is operable to connect with a plurality of remaining bone portions and connective tissue from the first hemi-pelvis.

9. The prosthetic device of claim 1, wherein the catch plate slides relative to the clamping portion and holds the pubis bone of the second hemi-pelvis between said catch plate and said clamping portion.

10. A prosthetic device for at least partial replacement of a first hemi-pelvis of a pelvis of a patient that defines a sagittal plane through the pelvis so a second hemi-pelvis is on a side of the sagittal plane opposite the first hemi-pelvis, the prosthetic device comprising:
    an acetabular component operable to replace at least a portion of the first hemi-pelvis;
    an ilium member attached to said acetabular component and operable to attach to remaining portions of a healthy ilium associated with the first hemi-pelvis; and
    a pubis member connected to said acetabular component, said pubis member including a clamping portion and a catch plate that is moveable relative to the clamping portion, said clamping portion and said catch plate being operable to directly connect to an opposed pubis bone of the second hemi-pelvis on the side of the sagittal plane that is opposite said acetabular component by holding said opposed pubis bone between said catch plate and said clamping portion.

11. The prosthetic device of claim 10, wherein said pubis member includes a worm drive that advances said catch plate toward said clamping portion to hold the opposed pubis bone of the second hemi-pelvis.

12. The prosthetic device of claim 10, wherein said acetabular component is configured to connect to a prosthetic femoral head.

13. The prosthetic device of claim 10, wherein said acetabular component is configured to connect to a natural femoral head.

14. The prosthetic device of claim 10, further comprising an acetabular cup configured to connect to said acetabular component.

15. The prosthetic device of claim 10, wherein the catch plate slides relative to the clamping portion and holds the pubis bone of the second hemi-pelvis between said catch plate and said clamping portion.

16. A method of replacing at least a portion of a first hemi-pelvis of a pelvis that defines a sagittal plane with a prosthetic device by connecting to a second hemi-pelvis that is on an opposite side of the sagittal plane from the first hemi-pelvis, of the method comprising:
    imaging at least a first portion of the first hemi-pelvis of the pelvis;
    constructing the prosthetic device based on said imaging of at least the first portion of the first hemi-pelvis;
    resecting a second portion of the first hemi-pelvis such that connective tissues are still attached to a remainder of the first hemi-pelvis;
    forming anatomical connection points on said prosthetic device to substantially match said remainder of the first hemi-pelvis;
    implanting said prosthetic device that is operable to replace at least the portion of the first hemi-pelvis but not any portion of the second hemi-pelvis;
    connecting a pubis member of said prosthetic device to an opposed pubis bone of the second hemi-pelvis on the opposite side of the sagittal plane from the first hemi-pelvis;
    connecting said connection points on said prosthetic device to said remainder of the first hemi-pelvis on a side of the sagittal plane opposite the second hemi-pelvis.

17. A method of replacing at least a portion of a first hemi-pelvis of a pelvis with a prosthetic device comprising:
    making an incision;
    removing at least a portion of a first hemi-pelvis of the pelvis from the patient that defines a sagittal plane;
    implanting the prosthetic device to replace at least the portion of the first hemi-pelvis but not a portion of a second hemi-pelvis;

connecting a pubis member of the prosthetic device to an opposed pubis bone of the second hemi-pelvis of the pelvis on a side of the sagittal plane opposite the first hemi-pelvis; and rotating a worm drive to clamp said pubis member of the prosthetic device to said opposed pubis bone of the second hemi-pelvis.

18. The method of claim 17 further comprising securing an acetabular cup in an acetabular component operable to provide an acetabulum for the first hemi-pelvis.

19. The method of claim 18 further comprising connecting a prosthetic femoral head to said acetabular cup.

20. The method of claim 17 further comprising securing a connecting flange on the prosthetic device to the first hemi-pelvis of the pelvis with one of bone screws and bone cement.

21. A prosthetic device for replacement of at least a portion of a first hemi-pelvis of a pelvis defining a sagittal plane by connecting to a second hemi-pelvis of the pelvis on a side of the sagittal plane opposite the first hemi-pelvis, the prosthetic device comprising:

a pubis member connected to an acetabular component, said acetabular component operable to provide a replacement for an acetabulum of the first hemi-pelvis;

a clamping portion connected to said pubis member and configured to connect to an opposed pubis bone of the second hemi-pelvis on the side of the sagittal plane opposite the first hemi-pelvis; and a catch plate opposite said clamping portion, said catch plate is operable to slide toward the clamping portion and hold the pubis bone of the second hemi-pelvis between said catch plate and said clamping portion to fixedly connect the prosthetic device that at least partially replaces the first hemi-pelvis to the second hemi-pelvis on the side of the sagittal plane opposite where the prosthetic device provides the replacement of the acetabulum of the first hemi-pelvis.

* * * * *